US012622595B2

(12) United States Patent
Frachi

(10) Patent No.: US 12,622,595 B2
(45) Date of Patent: May 12, 2026

(54) ELECTRODERMAL APPARATUS

(71) Applicant: OVOMIND SA, Plan-les Ouates (CH)

(72) Inventor: Yann Frachi, Marseilles (FR)

(73) Assignee: OVOMIND SA, Plan-les Ouates (CH)

( * ) Notice: Subject to any disclaimer, the term of this patent is extended or adjusted under 35 U.S.C. 154(b) by 518 days.

(21) Appl. No.: 18/027,747

(22) PCT Filed: Sep. 23, 2021

(86) PCT No.: PCT/IB2021/058697
§ 371 (c)(1),
(2) Date: Mar. 22, 2023

(87) PCT Pub. No.: WO2022/064425
PCT Pub. Date: Mar. 31, 2022

(65) Prior Publication Data
US 2023/0371837 A1 Nov. 23, 2023

(30) Foreign Application Priority Data

Sep. 23, 2020 (FR) ...................................... 2009668

(51) Int. Cl.
*A61B 5/0533* (2021.01)
*A61B 5/00* (2006.01)
*A61B 5/0205* (2006.01)
*A61B 5/16* (2006.01)

(52) U.S. Cl.
CPC ........ *A61B 5/0533* (2013.01); *A61B 5/02055* (2013.01); *A61B 5/165* (2013.01); *A61B 5/4035* (2013.01)

(58) Field of Classification Search
CPC ... A61B 5/0533; A61B 5/02055; A61B 5/165; A61B 5/4035; A61B 5/02416; A61B 5/721
See application file for complete search history.

(56) References Cited

U.S. PATENT DOCUMENTS

2013/0183646 A1 7/2013 Lusted et al.

FOREIGN PATENT DOCUMENTS

| FR | 3063425 | 9/2018 |
| KR | 20160085577 | 7/2016 |
| WO | 2017202626 | 11/2017 |

OTHER PUBLICATIONS

International Search Report and Written Opinion, Application No. PCT/B2021/058697, mailed Nov. 16, 2021 (28 pages).

(Continued)

*Primary Examiner* — Jonathan T Kuo
(74) *Attorney, Agent, or Firm* — Falcon Rappaport & Berkman LLP

(57) ABSTRACT
The invention presents an electrodermal apparatus comprising at least two electrodes (10), each of which is configured to be in contact with a dermal region, and an electronic circuit comprising an analog-to-digital converter and a processor that is configured to execute computer-executable instructions in order to bias the electrodes (10), to measure the current flowing between pairs of electrodes (10), to apply digital preprocessing to the measured electrical signals and to determine the conductance of the dermal layer, wherein the sensor further comprises an accelerometer, delivering electrical signals to the processor, the preprocessing taking into account the level of the signals that are delivered by the accelerometer.

5 Claims, 2 Drawing Sheets

(56) References Cited

OTHER PUBLICATIONS

Rui Guo et al., "Pervasive and unobtrusive emotion sensing for human mental health" 1-6, Pervasive Computing Technologies for Healthcare (Pervasivehealth), 2013 7th International Conference on IEEE, May 5, 2013, 4 pages.

Jorn Bakker et al., "What's Your Current Stress Level? Detection of Stress Patterns from GSR Sensor Data", Data Mining Workshops (Icdmw), 2011 IEEE 11th International Conference on IEEE, Dec. 11, 2011, 8 pages.

[Fig. 1]
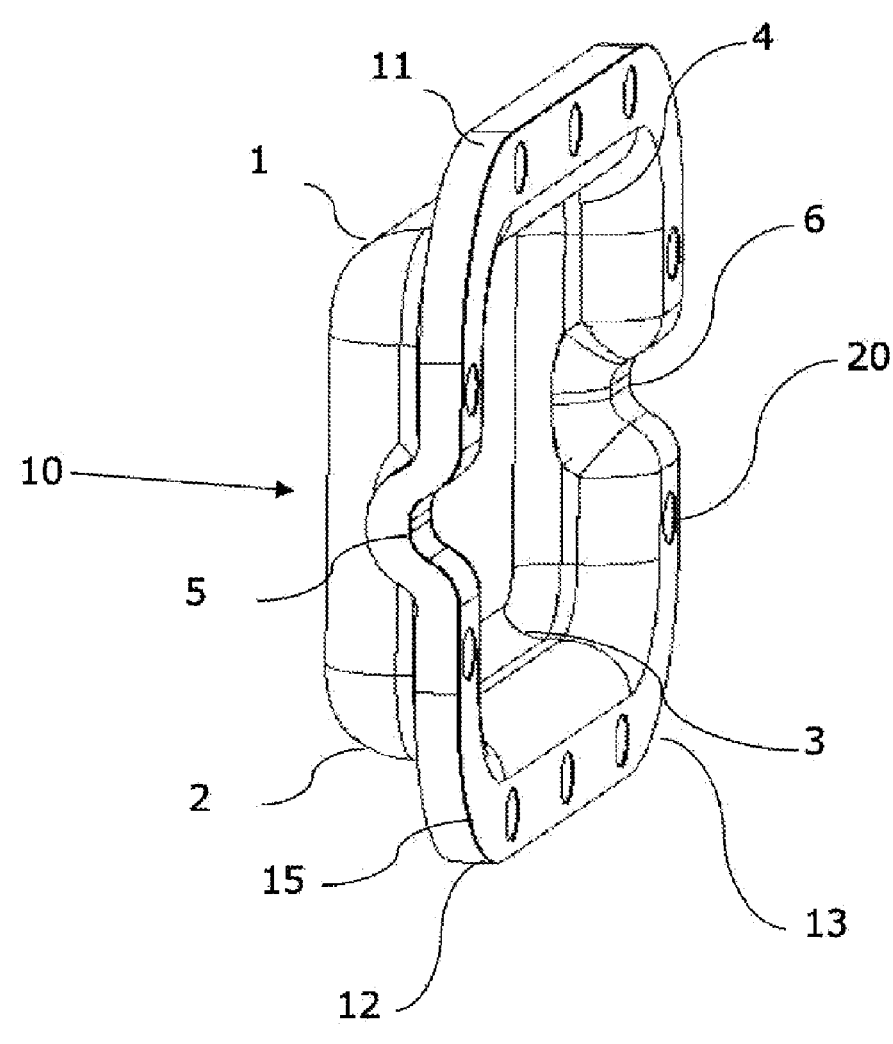

[Fig. 2]
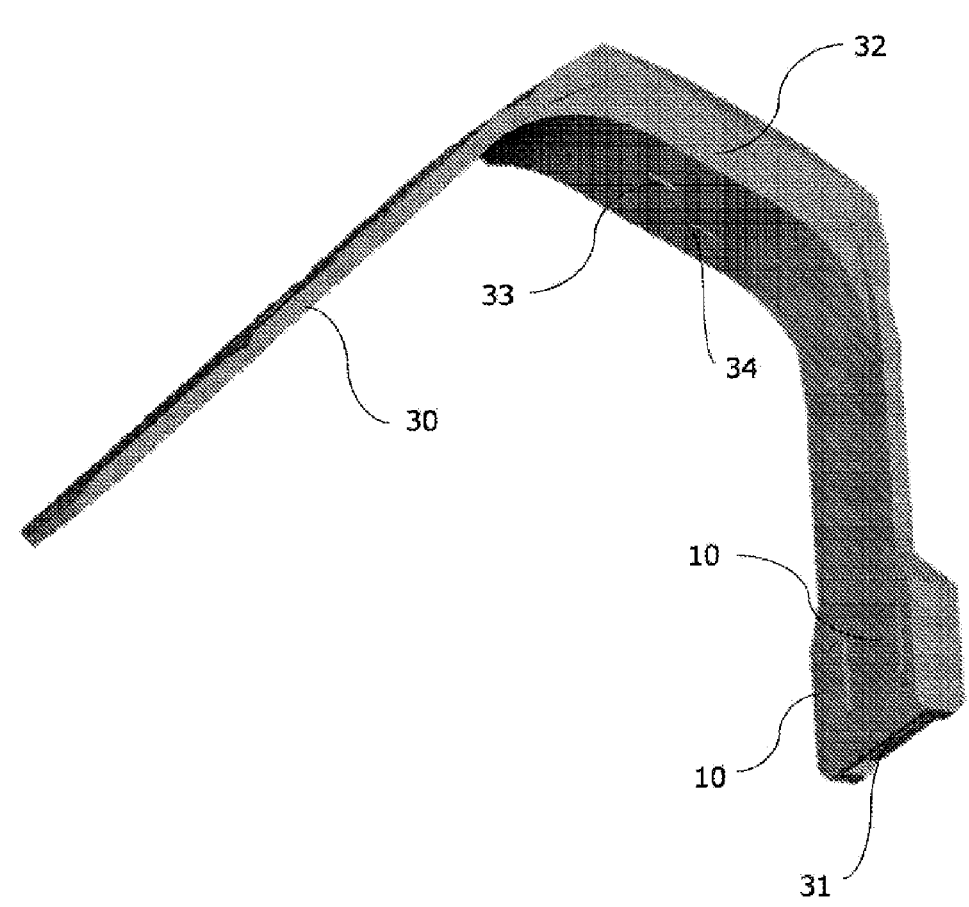

ELECTRODERMAL APPARATUS

CROSS REFERENCE TO RELATED APPLICATIONS

This application is the U.S. National Stage of International Application Number PCT/IB2021/058697 filed on Sep. 23, 2021, which application claims priority under 35 USC § 119 to French Patent Application No. 2009668 filed on Sep. 23, 2020. Both applications are hereby incorporated by reference in their entirety.

FIELD OF THE INVENTION

The present invention relates to the field of measuring galvanic skin response and electro-cutaneous activity, and in particular to portable devices and methods for measuring the electrodermal activity of the skin of a user.

Background of the Invention

Electrodermal activity is a biological electrical activity recorded on the surface of the skin and reflecting the activity of the sweat glands and of the autonomic nervous system, and consequently, inter alia, the individual's perception and subconscious behavior rather than that of a response that the individual wishes to give.

The scientific study of the galvanic skin response began in the early 1900s. The psychologist C. G. Jung is among the first to use its recording in psychoanalysis and he discusses this experiment in his publication "Studies in Word Analysis" published in 1962. Wilhelm Reich also studied the electrodermal response in experiments conducted at the Institute of Psychology of the University of Oslo, in 1935 and 1936, with the aim of confirming the existence of a bioelectric charge behind his concept of "vegetative currents of pleasure".

In the 1960s and until the end of the 1970s, the psychogalvanic response was used in all the fields of psychology for a wide variety of research. Psychogalvanic phenomena are linked to the activity of the sympathetic nervous system, and are manifested by the variation in the electrical resistance of the skin, after an emotion.

Many studies have focused on the exploitation of GSR (Galvanic Skin Response) or EDR (electrodermal resistance) signals representative of the variation in the electrical resistance of the skin caused by the activity of the sweat glands following a sensory excitation, called psychogalvanic reflex, for various applications such as lie detectors, emotion analysis, or controlling video games using new human-machine interfaces.

Prior Art

Patent FR3063425 proposes a system for determining an emotion of a user comprising a sensor to sense the electrodermal activity of the user, a first circuit adapted to:

a/ detect strong emotional moments felt by the user as a function of an analysis of information from the sensor (of electrodermal activity, b/ if a strong emotional moment is detected in step /a/, ask the user to classify said strong emotional moment.

This solution requires learning at the initiative of the user, who must identify a "strong emotional moment" and then classify it. It is quite obvious that this solution leads to erratic or even fanciful behaviors, and is in no way reproducible or reliable since it depends on the user's subjective experience, on their ability to properly complete this learning, and on the nature of the events to which the user is exposed during this learning phase.

Patent application WO2017202626 relates to a sensor intended to measure the conductance of the skin. An amplifier is used to convert the conductance of the skin into an analog output voltage which is then converted into the digital domain, so that the increase in the conductance of the tonic skin and the conductance response of the phasic skin are obtained in the digital domain. The amplifier has a nonlinear logarithmic gain, with a decreasing gain in order to increase the conductance values of the skin. The sensor makes it possible to detect both the increase of the tonic and phasic signals over a wide range of conductance of the skin. It allows optimum use of the analog-digital converter so that a lower resolution and therefore a less expensive converter can be used.

Patent application US 2013/183646 describes an apparatus for interoperable use of several data from biosensors attached to the user's finger. These sensors may be electrodermal response (EDR) sensors, or photoplethysmograph (PPG) signals, or temperature signals, or three-axis acceleration signals, and combinations thereof. The biometric card saves and processes the signals from the sensors and communicates them to a mobile device that interoperably uses several sensor information to determine aspects of the emotional state of the user.

The article "RUI GUO ET AL: "Pervasive and unobtrusive emotion sensing for human mental health", PERVASIVE COMPUTING TECHNOLOGIES FOR HEALTHCARE (PERVASIVEHEALTH), 2013 7TH INTERNATIONAL CONFERENCE ON, IEEE, May 5, 2013 (2013 May. 5), pages 436-439, XP032439656. DOi: 10.4108/ICST.PERVASIVEHEAL TH.2013.252133, ISBN: 978-1-4 799-0296-5.

Another article JORN BAKKER ET AL: "What's Your Current Stress Level? Detection of Stress Patterns from GSR Sensor Data", DATA MINING WORKSHOPS (ICDMW), 2011 IEEE 11 TH INTERNATIONAL CONFERENCE ON, IEEE, Dec. 11, 2011 (2011 Dec. 11), pages 573-580, XP032100119, DOi: 10.1109/ICDMW.2011.178, ISBN: 978-1-46733-0005-6 relates to stress detection phenomena.

Patent KR20160085577 is also known, describing another solution for determining a psychological state according to one embodiment of the present invention, which comprises: a bio-signal acquisition unit for acquiring a first bio-signal and a second bio-signal of a user generated by a first stimulus; and a psychological state determination unit for extracting a first characteristic and a second characteristic by analyzing the first bio-signal and the second bio-signal and by determining the psychological state of the user based on the first characteristic and the second characteristic. The first bio-signal and the second bio-signal are bio-signals indicating changes in the autonomous nerves measured by different biosensors. For example, the first bio-signal is a PPG signal measured by a pulse wave sensor, and the second bio-signal is a GSR signal measured by a skin conductivity sensor.

SUMMARY OF THE INVENTION

Solution Provided by the Invention

In order to remedy the drawbacks of the solutions of the prior art, the present invention relates in its most general sense to a system according to claim 1.

The system preferably comprises an electrodermal apparatus, for example an electrodermal bracelet comprising at least two electrodes, each of which is configured to be in contact with a dermal region, and an electronic circuit comprising an analog-to-digital convertor and a processor that is configured to execute computer-executable instructions in order to bias said electrodes, to measure the current flowing between pairs of electrodes, to apply digital preprocessing to the measured electrical signals and to determine the conductance of the dermal layer, characterized in that said accessory further comprises an absolute movement accelerometer and absolute rotation gyroscope (IMU), delivering electrical signals to said processor, said preprocessing taking into account the level of said signals that are delivered by said accelerometer and gyroscope simultaneously.

Advantageously, said electrodes are formed by studs formed by a stamped and tin-plated steel sheet.

Optionally, at least one of said electrodes has a housing capable of receiving an additional sensor.

According to one variant, said electrodermal apparatus further comprises a temperature sensor.

Advantageously, the temperature sensor is positioned on another dedicated steel probe or electrode. The thickness of this dedicated probe is specific in order to avoid too much inertia in the signal and to lose significant micro-variations in monitoring emotional reactions.

According to another variant, the electrodermal apparatus further comprises a heart rate sensor, preferably a heart rate sensor delivering physiological signals by photoplethysmography (PPG). The heart sensor is positioned under a piece of glass (PPG) and is not bonded to the metal electrode.

Techniques applicable to the PPG signal comprise:

techniques such as SVD and ICA which only exploit a single PPG channel and therefore provide relatively "poor" information but can be tested very quickly.

Fourier Series Analysis with automatic determination of the number of coefficients to be retained (as for ICA) is a technique that can be considered, but is rather complex due to the noise induced by the movements that may in certain transient circumstances be more powerful than the PPG signal.

The Periodic Moving Average Filter can be efficient but will induce a lot of latency in the signal.

Wavelet Denoising constitutes an effective alternative to the other methods.

The "Active Noise Cancellation" technique based on adaptive filtering is the method that seems to be the most appropriate to our multimodal approach and can be combined with Empirical Mode Decomposition to further improve denoising.

The invention also relates to a system comprising an electrodermal sensor according to at least one of the preceding variants and a computer delivering at least one item of digital data representative of an emotional state, characterized in that said computer executes a program controlling:

The processing of the digital conductance data provided by said processor over a sliding time window, the result of which provides a value $S_{arousal}$.

Advantageously, it further comprises a step of processing said second series of heart rate signals consists of bandpass filtering of the frequencies between 0.04 and 0.26 Hz and detecting peaks and measuring the time between the peaks RR, over said sliding time window, the result of which provides a value $S_{valence}$.

Detailed Description of a Non-Limiting Example of the Invention

BRIEF DESCRIPTION OF THE DRAWINGS

FIG. 1 shows a perspective view of an electrode according to the invention

FIG. 2 shows a partial view of a bracelet provided with two sensors according to the invention.

DETAILED DESCRIPTION

Hardware Architecture

The invention relates to a device for acquiring physiological signals by means of two (or more) electrodes in contact with the epidermis of a user, and the exploitation of different types of signals for estimating a reliable emotional state independent of artifacts such as the movements of the user. The spacing between the electrodes is important and determined, so that the quantity of skin through which the signal passes is sufficient to have an exploitable signal. Typically a spacing of 2 to 20 millimeters is suitable.

The invention implements two metal electrodes, of which [FIG. 1] is an example in perspective view.

An electrode is formed by stamping a stainless steel sheet, for example INOX 316L with a thickness of 0.5 millimeters to form an electrical pad (10) with a height of 2 millimeters, and 11 millimeters long, 8 millimeters wide, having a rectangular cross section with corners (1 to 4) rounded with a radius of curvature of 1.5 millimeters, extended by a border (15) of rectangular section with a width of 1.5 millimeters, with corners (11 to 13) rounded with a radius of curvature of 3 millimeters. The radius of curvature of the edges is 0.3 millimeters. The edge is pierced with holes (20) with a section of 0.8 millimeters for fastening on a bracelet or a support plate. Notches (5, 6) of semi-circular section with a radius of 1.1 millimeters allow electrical cables to pass through. The outer surface of the electrode is in contact with the epidermis and makes it possible, with a second electrode placed nearby, to measure the observed electrical conductivity at the surface of the user's skin and provide a signal representative of the electrodermal activity (EDA)

The electrode (10) may optionally integrate a plurality of sensors for obtaining measurements of physiological signals associated with the user's emotions, for example:

a sensor capable of measuring a heart rate of the user via a light formed in the metal electrode, and a window closing said light.

a sensor capable of measuring the surface temperature of the skin attached to the bottom by a thermal adhesive a sensor consisting of a three-axis or multi-axis accelerometer such as a 9-axis inertial module that is able to allow the measurement of movements on a limb of the user, for example a piezoelectric accelerometer or a three-axis MEMS accelerometer and a gyroscope (wrist rotation)

The signals supplied by the accelerometer are representative of the movements of the user and can be used to filter the physiological signals in order to eliminate the transient signals during sudden movements, which may alter the electrical conduction or the positioning of the electrode on the epidermis. This noisy signal filtering functionality is particularly important when the physiological signals are analyzed over a long time window, lasting several seconds, since the taking into account of abnormal signals would significantly falsify the evaluations produced by these time analyses.

Bracelet Details

FIG. 2 shows an example of mounting two 8×5 millimeters electrodes (10) having a thickness of 0.5 millimeters, arranged transversely, with a spacing of 10 millimeters, on a bracelet (30). The bracelet has a clasp (31) and a housing (32) for receiving the electronic circuits. The assembly may be overmolded to ensure insensitivity to moisture and dust.

The bottom of this zone has a temperature sensor (33) and an optical sensor (34) comprising a photodiode and LEDs for capturing blood flow-related signals, for example heart rate and oxygenation rate.

The electrodes are spaced apart and biased by an electronic circuit implementing an ADC LTC2487 ANALOG DEVICES (trade name) converter circuit comprising two differential inputs and ensuring 16-bit sampling as well as a temperature compensation circuit. It is also possible to use the ADC of the Nordic nRF52 microcontroller, which makes it possible to have two signal modes with the same components. This sensor makes it possible to measure the resistance of the skin via two dividing bridges at the input of an analogue to digital converter (ADC) in differential from a common point and to measure the voltage induced by the variation in the resistance of the human body, typically between 500 and 300 Ohm.

Sensors Equipping the Bracelet

The bracelet (30) can be equipped with several sensors:
a. A galvanic sensor using the two electrodes (10) providing a "galvanic skin response" signal sampled at 8 Hz, used by the computer to characterize the Arousal score and the vigilance level
b. A 3-axis accelerometer sampled at 64 Hz, used by the computer to characterize the pitches and falls.
c. A blood sensor (34) sampled at 50 Hz, used by the computer to characterize the valence score, biometric recognition, heart rate and stress level
d. A temperature sensor (33) sampled at 1 Hz for measuring the temperature of the body.

The bracelet comprises a computer for preprocessing the data which are then transmitted in the form of digital packets via a radiofrequency protocol by a radio module and an antenna.

Processing of Sampled Signals

Various types of processing may be considered to provide emotional analytics.

Fourier Series Analysis is a common solution, but entails a constraint relating to the automatic determination of the number of coefficients to be retained. This constraint is rather complex as the noise induced by the movements might be more powerful than the PPG signal, though without being present continuously. However, the use of a denoising solution based on the filtering of the signals according to the information provided by the accelerometer makes it possible to reduce this difficulty.

The sensor provides a signal representative of a passive or endosomatic parameter corresponding to the skin conductance level (SCL) or an active or exosomatic parameter corresponding to the skin conductance response (SCR). These parameters make it possible to determine the electrodermal activity (EDA) found in the characteristics of the epidermal membrane, and in the eccrine sweat activity under the control of the autonomic and central nervous systems.

There are two methods of recording.

The first one, called the endosomatic method, translates the potential differences generated by the skin membranes and leads to the measurement of the electrodermal potential. In this case, the sensor is a skin conductivity sensor associated with a current-voltage converter, for example a skin resistivity sensor, provided with a pair of noble steel electrodes.

The second one, called the exosomatic method, translates the variations of a current applied to the skin, the characteristics of which can lead to the measurement of various electrodermatical signals including skin conductance measurement, the one most commonly used in the literature.

Each of the electrodermatical signals is subdivided into a tonic component and a phasic component.

The first identifies the slow variations in the electrodermal signal while the second corresponds to the rapid variations in the signal commonly called electrodermal responses. Different measurement parameters can be extracted from these phase measurements, such as the frequency, latency or amplitude of the electrodermal responses. The origins and also the variability of the electrodermal activity measurement parameters make this activity sensitive to changes in our environment and to different mental processes under the control of the central nervous system, such as emotion, motivation or attention, and mental load.

Each sensor is associated with a preprocessing circuit optionally performing an analog processing (preempting, filtering, delivering an excitation signal), digitizing (sampling, optional digital filtering, storage in a buffer memory, etc.) to deliver digital signals to a computer that are used to determine the pair of values representative of the emotional state.

Processing the Physiological Signals

The signals supplied by an electrode pair are sampled at a frequency of 64 Hz, or even 130 Hz, and filtered in amplitude and frequency to remove aberrant signals. These signals constitute environmental information that supplements the signals associated with emotions, for example to give a context of a mode of movement and/or fall delivered by the accelerometer.

The signals supplied by the electrical conductivity sensor (10) are sampled at a frequency of 8 Hz and then processed for the calculation of the arousal score and the vigilance level.

The signals supplied by the heart rate sensor of the user are sampled at a frequency of 100 Hz and used by the computer for determining the valence score, as well as for biometric recognition and to estimate the stress level.

The skin temperature measurement sensor is sampled at a low frequency of around 1 Hz and completes the information that makes it possible to characterize the emotional state.

Example of a Particular Embodiment

One example embodiment consists of equipping the patient with a wireless connected bracelet equipped with three physiological sensors (a single sensor may suffice) measuring the electrodermal conductance (denoted GSR for galvanic skin response) at a rate of 8 Hz, the cardiac activity (PPG for photoplethysmography) at a rate of 50 Hz, the body temperature (denoted SKT for skin temperature) at a rate of 1 Hz and one or several accelerometric and gyroscopic sensors (denoted ACC) at a rate of 50 Hz are used to synchronously record the corresponding data and time-stamps.

The GSR and PPG data are transmitted to a mobile terminal that performs the computations for the real-time identification of the emotional state. The GSR and PPG data are stored in calculation buffers, the durations of which vary according to the calculated variables.

In each buffer memory, the signal processing is performed before the extraction of the different variables used for the identification analysis of the emotional state:
GSR signal: Bandpass filtering ($4^{th}$-order Butterworth) is applied to the signal with a bandwidth of 0.05-1 Hz.
PPG signal: Bandpass filtering ($4^{th}$-order Butterworth) is applied to the signal with a bandwidth of 0.5-5 Hz.

The variables used for the identification analysis from the emotional state are then extracted from the processed signals. The variable Arousal is obtained in a 20-second computation buffer memory from the normalized spectral power of the GSR signal calculated over the 0.045-0.25 Hz band by a Hilbert-Huang transformation.

7

8

Example of Processing

The variable Mdiff is recorded in a 2-second computation buffer from the average of the absolute value of the first derivative of the GSR signal.

The variable Valence is obtained in a 60-second computation buffer by calculating the cardiac coherence ratio. For this, a detection of the peaks in the PPG signal is carried out from a dedicated function to deduce therefrom the peak-to-peak time intervals, denoted RR intervals. Then, the heart rate noted BPM is calculated from RR intervals.

From the signal BPM, the maximum peak of the power spectrum is identified on the 0.04-0.26 Hz band (the frequency range within which the coherence can be observed). The power of this peak, denoted Peak Power, is then determined by calculating the integral on a width of 0.030 Hz, centered around the peak. The total power on the 0.0033-0.4 Hz band of the BPM signal noted Total Power is then calculated. The normalized valence level is obtained by the following calculation:

$$\text{Valence} = \frac{\text{Peak Power}}{\text{Total Power} - \text{Peak Power}} \qquad (1)$$

Every second, the new GSR and PPG values recorded by the bracelet make it possible to calculate the new Arousal, Mdiff and Valence.

Mdiff is stored in memory in the last minute to allow dynamic calibration of the system for detecting spot variations of the physiological excitation level. A weighting coefficient is applied to these calibration data in order to make the contribution of the most recent values larger during calibration. It is then possible to calculate the dynamic thresholds, making it possible to classify the variable, respectively Mdiff. The calculation of the thresholds can be detailed in the following way:

$$\text{Threshold}_{(t)} = \frac{\text{Max}\left(Mdiff\begin{bmatrix} x_1 \\ \vdots \\ x_n \end{bmatrix}\right) + \text{Mean}\left(Mdiff\begin{bmatrix} x_1 \\ \vdots \\ x_n \end{bmatrix}\right)}{2} \qquad (1)$$

Where $\text{Threshold}_{(t)}$ represents the value of the dynamic threshold at the time t and $$Mdiff\begin{bmatrix} x_1 \\ \vdots \\ x_n \end{bmatrix}$$

represents the values of the variable Mdiff over the entire duration of the calibration period.

Each second, a new value of Threshold is obtained and compared to Mdiff. If Mdiff is greater than its threshold value, then an emotional reaction is detected.

Other Processing Modes

The processing according to the "Periodic Moving Average Filter" solution can be effective, but induces a lot of latency in the signal.

"Wavelet Denoising" processing is a relevant solution, as well as the "Active Noise Cancellation" processing based on adaptive filtering. It is the most appropriate method for a multimodal approach and can be combined with an "Empirical Mode Decomposition" processing to further improve the denoising.

Specific Processing Examples

The purpose of the invention is to provide digital signals $S_{arousal}$ and $S_{valency}$ representative of the emotional state of a person, automatically and without intervention by a human.

Efficient recognition of emotions from human physiological activity can be achieved using a simple emotional model. Indeed, the emotions can be projected in a multidimensional space, the most common being the valence-awakening plane. The valence level represents the positivity and negativity of an emotion while the awake level describes the intensity of the emotion. These two emotional components are expressed at the physiological level.

During stress, the sympathetic nervous system predominates and leads to an elevation of the physiological awakening level. An acceleration of the heart rate or an acceleration of the inter-beat interval (IBI) is characteristic of this state. Denoising is all the more important for this indicator from which the Valence results. Light is more sensitive to movements (PPG).

At rest, on the contrary, the parasympathetic nervous system activates a reduction in the physiological waking state and heart rate. Furthermore, the alternation of accelerations and decelerations of the heart rate becomes regular and coherent (state of cardiac coherence) in the states of wellness, calm, control (positive emotional valence) while in the states of stress, anxiety, anger (negative emotional valence), the tachogram corresponding to the pair $S_{arousal}$ and $S_{valence}$ becomes irregular, its chaotic plot and its magnitude will decrease.

By extracting from the PPG signal the level of coherence of the heart rate, it becomes possible to obtain a robust indicator of the emotional valence level and to calculate dynamic thresholds above which this valence level significantly changes.

Once the valence level has been estimated, it is then possible to verify the level of wakefulness by controlling in the spectral domain the physiological activation level from the GSR signal to deduce therefrom the emotional state of the individual in real time and communicate it to the multimedia system with which the latter interacts.

The emotional state can be characterized according to the following table:

TABLE 1

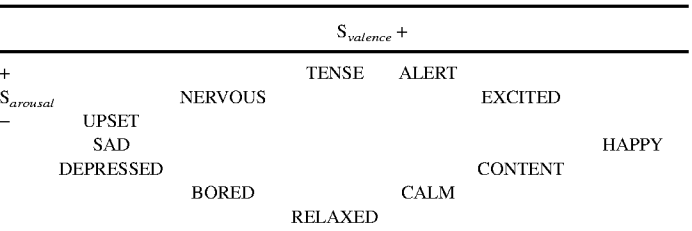

| | | | $S_{valence}$ + | | | |
|---|---|---|---|---|---|---|
| + | | | TENSE | ALERT | | |
| $S_{arousal}$ | | NERVOUS | | | EXCITED | |
| – | UPSET | | | | | |
| | SAD | | | | | HAPPY |
| | DEPRESSED | | | | CONTENT | |
| | | BORED | | CALM | | |
| | | | RELAXED | | | |

During stress, the sympathetic nervous system predominates and leads to an elevation of the physiological awakening level. An acceleration of the heart rate is characteristic of this state. At rest, on the contrary, the parasympathetic nervous system activates a reduction in the physiological waking state and heart rate. Furthermore, the alternation of accelerations and decelerations of the heart rate becomes regular and coherent (state of cardiac coherence) in the states of wellness, calm, control (positive emotional valence) while in the states of stress, anxiety, anger (negative emotional valence), the tachogram becomes irregular, its chaotic plot and its magnitude will decrease.

By extracting from the PPG signal the level of coherence of the heart rate, it becomes possible to obtain a robust indicator of the emotional valence level and to calculate dynamic thresholds above which this valence level significantly changes.

Once the valence level has been estimated, it is then possible to verify the level of wakefulness by controlling in the spectral domain the physiological activation level from the GSR signal to deduce therefrom the emotional state of the individual in real time and communicate it to the multimedia system with which the latter interacts.

Training Characterization Criteria

To build a characterization model, the invention proposes a variant implementing a preparatory supervised learning step.

This solution consists of proposing to a panel of users equipped with a device for acquiring the aforementioned physiological data, experiment plans formed by a succession of video sequences labeled emotional associated each with a digital descriptor ID (t), and recording the pairs of signals $S_{arousal}$ and $S_{valence}$ and their evolution over time, for each of the members of the panel.

These structured data ($S_{arousal}$ and $S_{valence}$ (t); ID (t)) for each of the members of the panel are then introduced into a neural network, to produce a characterization model.

Participants will be equipped with a connected bracelet according to the invention equipped with three physiological sensors measuring cardiac activity (PPG for photoplethysmograph), body temperature (denoted SKT for skin temperature) and electrodermal conductance (denoted GSR). The bracelets communicate with a portable acquisition computer making it possible to synchronously register the corresponding data and timestamp with an acquisition frequency of 50 Hz, 1 Hz and 4 Hz for the PPG, the SKT and the GSR, respectively for the connected bracelet or connected watch and with an acquisition frequency of 64 Hz, 4 Hz and 4 Hz for the PPG, the SKT and the GSR.

An HTC Vive virtual reality system will be used to display the selected stimuli to induce an emotional reaction and makes it possible to have additional immersion (unprecedented in emotional stimulation protocol)

Experimental Design

For each participant, the data will be saved in a single session of twenty minutes. The experiment plan is: Sn (participants)*V6 (six emotional videos).

Each video corresponds to an emotional extreme:

Video 1: Rest (40 s)—Emotional induction phase for sadness (30 s)—Post-effect (30 s)

Video 2: Rest (40 s)—Emotional induction phase for joy (30 s)—Post-effect (30 s)

Video 3: Rest (40 s)—Emotional induction phase for disgust (30 s)—Post-effect (30 s)

Video 4: Rest (40 s)—Emotional induction phase for fear (30 s)—Post-effect (30 s)

Video 5: Rest (40 s)—Emotional induction phase for neutral (30 s)—Post-effect (30 s)

Video 6: Rest (40 s)—Emotional induction phase for relaxation (30 s)—Post-effect (30 s)

The rest phase will constitute a baseline period in order to initialize the calculation of the physiological variables. For each participant, the order of presentation of the videos will be random in order to avoid any ordering effect. In addition, in order to enrich the dataset, two videos will be available for the emotions of fear and joy. For each participant, the choice of the video used for each of these two emotions will be random.

Data Acquisition Procedure

Each participant is first equipped with one or more connected bracelets and a virtual reality system allowing them to isolate themselves from external stimulations and to optimize their attentional focus. The experimenter then checks the quality of the physiological signals. Each participant will have a general instruction to view six videos for 30 seconds. During the 40 seconds preceding the video and the 30 seconds after the video, the instruction given will be to keep calm and still. When all videos have been viewed, the experimenter helps the participant remove the virtual reality headset and the bracelet and then conduct a debriefing to check that all went well Data Analysis For each participant, the recorded physiological data will be preprocessed as follows:

For the PPG signal, the signal jumps will be corrected using a dedicated function. A bandpass filter (4th-order Butterworth) will then be applied to the signal with a bandwidth of 0.5-5 Hz, then the signal will be normalized using a Hilbert transform and smoothed using a Gaussian window of 16 seconds. As regards the signal SKT, a low-order filtering (4th-order Butterworth) will be applied to the signal with a cutoff frequency at 0.05 Hz. Finally, bandpass filtering (4th-order Butterworth) will be applied to the GSR signal with a bandwidth of 0.05-3 Hz. All of these variables will constitute the input data of the emotional classification algorithms.

Graphical Representation of the Processing Results

Every second, the variables obtained are represented by the display system of the detected emotional state (denoted the overlay) as follows:

The diameter of the circle corresponds to the normalized value of the value $S_{Arousal}$. The greater the diameter, the higher the level of arousal.

The color of the circle corresponds to the normalized value of the value $S_{Valence}$. When the color tends towards green, the valence level is higher. When the color tends towards red, the valence level is lower.

When an emotional reaction is detected from the evolution parameter Mdiff, the outline of the circle is animated. The value of the heart rate is updated at the center of the circle.

The emotional state is communicated to the multimedia system with which the individual interacts ([FIG. 2]). It is important to note that the dock/mobile provides for the updating of the bracelet on the one hand and the calculation methods of the values and the detection levels on the other hand via an Internet connection.

APPLICATIONS

The method according to the invention makes it possible to deliver control signals for controlling an apparatus such as a robot, in particular an empathetic robot or for controlling functional parameters of an electronic apparatus such as the sound level, light level, rhythm, etc.

These signals also make it possible to control the adaptation of the speed of an individual/collective transport vehicle and the management of the safety, control, pilot, and driving agents, but also the reduction in the amount of information in a situation where piloting is difficult (fighter jet or F1).

The invention claimed is:

1. A system comprising a computer and an electrodermal sensor comprising a blood sensor and at least two electrodes, each of which is configured to be in contact with a dermal region, and an electronic circuit comprising an analog-to-digital converter and a processor that is configured to execute computer-executable instructions in order to bias said electrodes, to measure the current flowing between pairs of electrodes, to apply digital preprocessing to the measured electrical signals and to determine the conductance of the dermal layer, said sensor further comprising an accelerometer, delivering electrical signals to said processor, said preprocessing taking into account the level of said signals that are delivered by said accelerometer, characterized in that said computer executes a program controlling:

the processing of the digital conductance data provided by said processor over a sliding time window, the result of which provides a value $S_{arousal}$ corresponding to an intensity of the emotion and processing of a series of heart rate signals consisting of bandpass filtering of the frequencies between 0.04 and 0.26 Hz and detecting peaks and measuring the time between the peaks RR, over said sliding time window, the result of which provides a value $S_{valence}$ corresponding to the positivity and negativity of the emotion.

2. The system according to claim 1, wherein said electrodes are formed by studs formed by a stamped steel sheet.

3. The system according to claim 1, wherein the system further comprises a temperature sensor.

4. The system according to claim 1, wherein the system further comprises a heart rate sensor.

5. The system according to claim 4, wherein said heart rate sensor delivers physiological signals by photoplethysmography.

* * * * *